(12) United States Patent
Jeong et al.

(10) Patent No.: US 8,791,301 B2
(45) Date of Patent: Jul. 29, 2014

(54) METHOD OF PREPARING SECONDARY AMINE COMPOUND USING MICROFLOW REACTOR

(75) Inventors: Jin-Hyun Jeong, Seoul (KR); Han-Seo Moon, Chungbuk (KR); Liu-Lan Shen, Liaoning (CN); Yong-Sung Choi, Seoul (KR)

(73) Assignee: University-Industry Cooperation Group of Kyunghee University, Yongin-si (KR)

(*) Notice: Subject to any disclaimer, the term of this patent is extended or adjusted under 35 U.S.C. 154(b) by 0 days.

(21) Appl. No.: 13/577,194

(22) PCT Filed: Feb. 1, 2011

(86) PCT No.: PCT/KR2011/000731
§ 371 (c)(1), (2), (4) Date: Feb. 6, 2013

(87) PCT Pub. No.: WO2011/096729
PCT Pub. Date: Aug. 11, 2011

(65) Prior Publication Data
US 2013/0137900 A1 May 30, 2013

(30) Foreign Application Priority Data
Feb. 4, 2010 (KR) ......................... 10-2010-0010432

(51) Int. Cl.
*C07C 211/00* (2006.01)

(52) U.S. Cl.
USPC ........................................... 564/307

(58) Field of Classification Search
None
See application file for complete search history.

(56) References Cited

U.S. PATENT DOCUMENTS 5,986,158 A * 11/1999 Van Broekhoven et al. .. 585/722
6,192,596 B1 * 2/2001 Bennett et al. ................... 34/76
6,423,871 B1 7/2002 Jung

FOREIGN PATENT DOCUMENTS

KR   1981-0000556 B1   6/1981
KR   2002-0072284 A    9/2002

OTHER PUBLICATIONS

Mason et al. Chem. Rev. 2007, 107, 2300-2318.*
Chang et al. Org. Lett, 2008, 10(6), 1163-1166.*
Chang et al. Org. Lett, 2008, 10(6), supplementary data, pp. 1-42.*
Baxter et al., "Reductive Aminations of Carbonyl Compounds with Borohydride and Borane Reducing Agents," Organic Reactions, vol. 59, p. 1, 2004. (Abstract only).

* cited by examiner

*Primary Examiner* — Clinton Brooks
(74) *Attorney, Agent, or Firm* — Seed IP Law Group PLLC

(57) ABSTRACT

Disclosed is a novel method of preparing a secondary amine compound using a microflow reactor. According to the method, a primary amine compound and a halide compound are allowed to react with each other in the microflow reactor, such that the production of a tertiary amine compound or an ammonium salt is minimized, whereby the secondary amine compound is efficiently prepared.

8 Claims, 1 Drawing Sheet

METHOD OF PREPARING SECONDARY AMINE COMPOUND USING MICROFLOW REACTOR

TECHNICAL FIELD

The present invention relates to a novel method of preparing a secondary amine compound using a microflow reactor.

BACKGROUND ART

A reaction to prepare a secondary amine compound or a tertiary amine compound from a primary amine compound using a halide compound is frequently used in laboratory or for industrial purposes. However, when a primary amine compound is allowed to react with a halide compound so as to prepare a secondary amine compound, the secondary amine compound can react with the halide compound to produce a tertiary amine compound or an ammonium salt, because the nucleophilicity of the secondary amine compound can be greater than that of the primary amine compound. Namely, when the primary amine compound is allowed to react with the halide compound according to a general method, a mixture of the secondary amine compound, the tertiary amine compound and the ammonium salt can be produced, and the separation of the secondary amine compound from the mixture can be time-consuming and cost-ineffective.

Various methods have been attempted to obtain a secondary amine compound from a primary amine compound while minimizing the production of byproduct such as a tertiary amine compound or an ammonium salt. For example, a reductive alkylation reaction is known in which a secondary amine compound is prepared by allowing a primary amine compound to react with aldehyde or ketone to produce an imine compound which is then reduced with a reducing agent such as sodium borohydride or sodium cyanohydride (Ellen W. Baxter and Allen B. Reitz, Reductive Aminations of Carbonyl Compounds with Borohydride and Borane Reducing Agents, Organic Reactions, 1, 59, 2002). However, this method has shortcomings in that the reducing agent should additionally be used and aldehyde or ketone should be used in place of the halide compound. Also, a method is known in which a secondary amine compound is produced from a primary amine compound using a base such as cesium hydroxide monohydrate, potassium carbonate or triethylamine, but this method has disadvantages of long reaction time and high production cost.

Accordingly, there is a need for a method capable of effectively synthesizing a secondary amine compound from a primary amine compound while minimizing the generation of a tertiary amine compound or an ammonium salt.

DISCLOSURE OF INVENTION

Technical Problem

It is, therefore, an object of the present invention to provide a method of effectively preparing a secondary amine compound from a primary amine compound and a halide compound while minimizing the generation of a tertiary amine compound or an ammonium salt.

Solution to Problem

According to the present invention, a secondary amine compound may be prepared using a system including a microflow reactor.

As used herein, the term microflow reactor refers to a reactor in which a chemical reaction is carried out in a space of micrometer scale or less. Preferably, the microflow reactor comprises microchannels so that reactants react with each other while they pass through the inside of the microchannels. The structure of the microflow reactor, etc., is described in, for example, U.S. Pat. Nos. 6,449,184, 6,228,434 or 6,192,596. The structure of the microflow reactor, described in the above US patents, may be applied to the present invention.

The inventive system including the microflow reactor may include storage units, a mixing unit, the microflow reactor, and flow channels that connect the storage units, the mixing unit and the microflow reactor with each other.

The storage units serve to store reactants before the introduction of the reactants into the microflow reactor.

The number of the storage units may be suitably controlled as required.

The mixing unit serves to uniformly mix the reactants, introduced from the storage units, so as to produce a mixture.

The reactants contained in the mixture, transferred from the mixing unit to the microflow reactor, react with each other in the microflow reactor. The microflow reactor comprises microchannels so that the reactants contained in the mixture may react with each other while they pass through the microchannels. By controlling the temperature and pressure of the microflow reactor and the residence time of the reactants in the microflow reactor, the yield of the final product and the production of byproducts can be controlled.

The flow channels serve to transfer reactants or a mixture thereof to the storage units, mixing unit or microflow reactor of the system. Depending on the flow rates of the reactants or mixtures in the flow channels and the lengths of the flow channels, the efficiency of the reaction which is carried out in the microflow reactor may be controlled.

The system including the microflow reactor may include, in addition to the above-described storage units, mixing unit and microflow reactor, a control unit for controlling the microflow reactor, and a collection unit for storing the final product.

A method of preparing a secondary amine compound using a microflow reactor according to the present invention includes the steps of: mixing a first reactant, comprising a primary amine compound represented by the following formula (1), with a second reactant comprising a halide compound represented by the following formula (2), thereby producing a mixture; and introducing the mixture into the microflow reactor through flow channels, thereby synthesizing a secondary amine compound represented by the following formula (3):

Formula (1): $R_1-NH_2$

Formula (2): $R_2-X$

Formula (3): $R_1-\overset{H}{N}-R_2$ wherein $R_1$ is a substituted or unsubstituted, linear or branched $C_1$-$C_6$ alkyl, a substituted or unsubstituted, linear or branched $C_2$-$C_6$ alkenyl, a substituted or unsubstituted $C_3$-$C_6$ cycloalkyl, a substituted or unsubstituted phenyl, or a substituted or unsubstituted naphthalenyl, $R_2$ is a substituted or unsubstituted, linear or branched $C_1$-$C_6$ alkyl, a substituted or unsubstituted, linear or branched $C_2$-$C_6$ alkenyl, a substituted or unsubstituted benzyl, or a substituted or unsubstituted methyl naphthalene, and X is chloro, bromo or iodo.

In the present invention, $R_2$ in formula (2) may be allyl, butyl, pentyl, butenyl, benzyl or pentenyl, and X may be bromo.

In the present invention, the step of mixing the first and second reactants to produce the mixture may include the steps of: introducing the first reactant and the second reactant into the storage units; and transferring the first reactant and the second reactant from the storage units to the mixing unit.

In the present invention, the primary amine compound may be represented by the following formula (4):

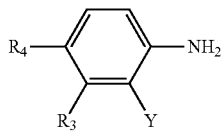

Formula (4)

wherein $R_3$ and $R_4$ are each independently H, a substituted or unsubstituted, linear or branched $C_1$-$C_6$ alkyl, a substituted or unsubstituted $C_2$-$C_3$ alkenyl, a substituted or unsubstituted phenyl, a substituted or unsubstituted naphthalenyl, a linear or branched $C_1$-$C_6$ heteroalkyl group containing at least one of O, N, S and Se, a $C_2$-$C_3$ heteroalkenyl group containing at least one of O, N, S and Se, or a $C_5$-$C_{12}$ heteroaryl group containing at least one of O, N, S and Se, and Y is H, fluoro, chloro, bromo, iodo, nitro, a substituted or unsubstituted phenyl, a substituted or unsubstituted naphthalenyl, or a substituted or unsubstituted, linear or branched $C_1$-$C_6$ alkyl.

In the present invention, when the primary amine compound represented by the formula (4) reacts with the halide compound represented by the formula (2), a secondary amine compound represented by the following formula (5) may be prepared:

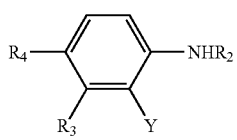

Formula (5)

wherein $R_2$ is a substituted or unsubstituted, linear or branched $C_1$-$C_6$ alkyl, a substituted or unsubstituted, linear or branched $C_2$-$C_6$ alkenyl, a substituted or unsubstituted benzyl, or a substituted or unsubstituted methyl naphthalene, $R_3$ and $R_4$ are each independently H, a substituted or unsubstituted, linear or branched $C_1$-$C_6$ alkyl, a substituted or unsubstituted $C_2$-$C_3$ alkenyl, a substituted or unsubstituted phenyl, a substituted or unsubstituted naphthalenyl, a linear or branched $C_1$-$C_6$ heteroalkyl group containing at least one of O, N, S and Se, a $C_2$-$C_3$ heteroalkenyl group containing at least one of O, N, S and Se, or a $C_5$-$C_{12}$ heteroaryl group containing at least one of O, N, S and Se, and Y is H, fluoro, chloro, bromo, iodo, nitro, a substituted or unsubstituted phenyl, a substituted or unsubstituted naphthalenyl, or a substituted or unsubstituted, linear or branched $C_1$-$C_6$ alkyl.

In the present invention, each of the first reactant comprising the primary amine compound and the second reactant comprising the halide compound may further comprise cesium hydroxide.

In the present invention, each of the first reactant comprising the first amine compound and the second reactant comprising the halide compound may comprise dimethylformamide, tetrahydrofuran, acetonitrile, methanol, ethanol, isopropanol or isobutanole, which may be used alone or in a mixture of two or more thereof.

In the present invention, the temperature of the microflow reactor in which the first reactant and the second reactant react with each other may be in the range of from 80° C. to 300° C. If the temperature of the microflow reactor is in the range of from 80° C. to 300° C., the yield of the secondary amine compound can be increased.

In the present invention, the flow rate of the mixture in each of the flow channels may be 0.01-10 ml/min, and preferably 0.01-5 ml/min. If the flow rate of the mixture in the flow channel is out of the above range, the diffusion rate of the reactants in a solution state can increase or the reaction time of the reactants can become shorter, thus making it difficult to induce an efficient reaction.

In the present invention, the first and second reactants may react with each other in the microflow reactor for 30 seconds to 10 minutes.

In the present invention, each of the first, second and third flow channels may have a length of 1-100 cm.

Advantageous Effects of Invention

According to the method of the present invention, the secondary amine compound can be efficiently produced by allowing the primary amine compound to react with the halide compound in the microflow reactor while minimizing the production of a tertiary amine compound or an ammonium salt.

BEST MODE FOR CARRYING OUT THE INVENTION

Figure 1:
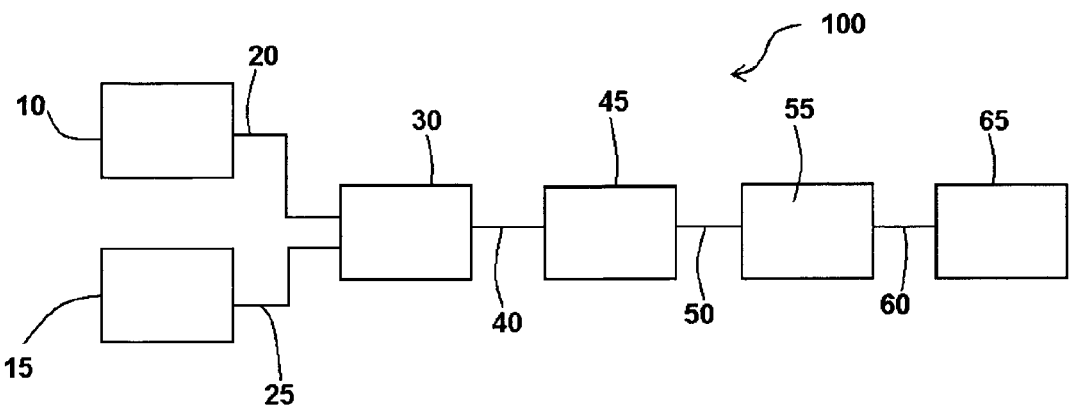
FIG. 1 is a schematic diagram illustrating a system including a microflow reactor, which is used to prepare a secondary amine compound according to embodiments of the present invention.

Hereinafter, preferred embodiments of the present invention will be described in detail with reference to the accompanying drawings. However, these drawings and embodiments are given only for a better understanding of the present invention and are not to be construed to limit the scope of the present invention. It is to be understood that the present invention include all modifications, equivalents, and alternatives falling within the spirit and scope of the present invention. In the drawings, the identical or similar reference numerals designate the identical or similar elements. It is to be understood that, although the terms first, second, etc. are be used herein to describe various elements, these elements should not be limited by these terms. These terms are used to distinguish one element from another, but not to imply a required sequence of elements. The terminology used herein is for the purpose of describing particular embodiments only and is not intended to be limiting of the present invention. As used herein, the singular forms are intended to include the plural forms as well, unless the context clearly indicates otherwise. It is to be further understood that the terms comprises, comprising, includes and/or including, when used herein, specify the presence of stated features, figures, steps, operations, elements, components or combination thereof, but do not preclude the presence or addition of one or more other features, figures, steps, operations, elements, components, and/or combinations thereof.

Hereinafter, a method for preparing a secondary amine compound of the present invention will be described in detail with reference to the accompanying drawings.

FIG. 1 is a schematic diagram showing a system including a microflow reactor, which is used in a method for preparing a secondary amine compound according to the present invention.

Referring to FIG. 1, a system 100 comprising a microflow reactor according to embodiments of the present invention comprises storage units 10 and 15, flow channels 20, 25, 40, 50 and 60, a mixing unit 30, a microflow reactor 45, a control unit 55, and a collection unit 65.

When the secondary amine compound is prepared using the system 100 comprising the microflow reactor, the desired secondary amine compound can be produced in large amounts at low cost using the system 100 including the microflow reactor without performing an additional experiment. By suitably adjusting the settings of the system including the microflow reactor, it is possible to accurately control the temperature and pressure of the microflow reactor 45, the residence time of the reactants in the reactor, and the flow rates of the reactants in the plurality of the flow channels. As a result, the yield of the secondary amine compound can be controlled, and the production of byproducts, including a tertiary amine compound or an ammonium salt, can be minimized. Accordingly, the secondary amine compound can be effectively prepared from the primary amine compound while minimizing the production of byproducts, unlike the case of synthesizing the secondary amine compound in a flask or the like.

The system 100 including the microflow reactor according to the present invention comprises storage units 10 and 15. The storage units 10 and 15 serve to store the reactants introduced into the system 100 including the microflow reactor.

According to embodiments of the present invention, the system 100 including the microflow reactor may comprise a first storage unit 10 and a second storage unit 15. The first and second storage units 10 and 15 may include a primary amine compound and a halide compound, respectively.

Although FIG. 1 shows the case in which the system 100 including the microflow reactor includes two storage units, that is, the first and second storage units 10 and 15, the number of the storage units that are included in the system 100 including the microflow reactor may be suitably controlled as required. For example, the system 100 may include a single storage unit in which all the reactants may be introduced.

According to embodiments of the present invention, the storage units 10 and 15 of the system 100 including the microflow reactor may comprise a pump capable of mixing the reactants and discharging the reactants from the storage units 10 and 15.

The system 100 including the microflow reactor comprises a plurality of flow channels 20, 25, 40, 50 and 60. The flow channels serve to connect the storage units 10 and 15, the mixing unit 30, the microflow reactor 45, the control unit 55 and the collection unit 65 with each other and to transfer the reactants and the reaction product of the reactants.

Accordingly to embodiments of the present invention, the system 100 including the microflow reactor may comprise a first flow channel 20, a second flow channel 25, a third flow channel 40, a fourth flow channel 50 and a fifth flow channel 60. The first flow channel 20 and the second flow channel 25 serve to transfer the reactants from the first and second storage units 10 and 15 to the mixing unit 30. The third flow unit 40 serves to transfer the reactants mixed in the mixing unit 30 to the microflow reactor 45. The fourth flow channel 50 serves to transfer the product from the microflow reactor 45 to the control unit 55. The fifth flow channel 60 serves to transfer the product from the control unit 55 to a collection unit. Although FIG. 1 shows the case in which the system 100 including the microflow reactor comprises the first to fifth flow channels 20, 25, 40, 50 and 60, the number and locations of the flow channels can be suitably controlled as required.

According to embodiments of the present invention, the yield of the final product and the production of byproducts can be controlled depending on the length of each of the first to third flow channels 20, 25 and 40 and on the flow rate of the reactants in each of the first to third flow channels 20, 25 and 40. Each of the first to third flow channels 20, 25 and 40 may have a length of 1-100 cm. Preferably, each of the first to third flow channels 20, 25 and 40 may have a length of 1-20 cm.

The system 100 including the microflow reactor comprises a mixing unit 30. The mixing unit 30 serves to mix the reactants, transferred from the storage units 10 and 15 through the first and second flow channels 20 and 25.

According to embodiments of the present invention, the first and second flow channels 20 and 25 are combined into one tube in the mixing unit 30, so that the reactants in the first and second flow channels 20 and 25 can be mixed with each other in the mixing unit 30.

The system 100 including the microflow reactor comprises a microflow reactor 45. The reactants transferred from the mixing unit 30 through the third flow channel 40 react with each other in the microflow reactor 45 to produce a product.

According to embodiments of the present invention, the microflow reactor 45 may include a plurality of microchannels. The arrangement, length and capacity of the microchannels can be suitably controlled depending on the type of reaction that is carried out in the microflow reactor 45. Preferably, the microflow reactor 45 may have either a configuration in which the microchannels are stacked on each other or a configuration in which the microchannels are arranged in parallel to have a specific shape.

The system 100 including the microflow reactor may comprise a control unit 55. The control unit 55 can serve to control reaction conditions and the like during the operation of the system 100 including the microflow reactor.

According to embodiments of the present invention, the control unit 55 can control the pressure of the system 100 including the microflow reactor. As a result of controlling the pressure of the system 100, the yield of the product can be increased either by controlling the equilibrium of the reaction which is carried out in the microflow reactor 45 or by controlling the heat generated from the reaction.

The system 100 including the microflow reactor comprises a collection unit 65. The collection unit 65 serves to store the product transferred through the fifth flow channel 60.

According to embodiments of the present invention, the system 100 including the microflow reactor may, if necessary, comprise other elements, or may additionally comprise the same elements as described above.

According to embodiments of the present invention, in the method of synthesizing the secondary amine compound from the primary amine compound and the halide compound, FRX 100, FRX 200, FRX 300 or FRX 400, which are commercially available from Syrris Limited, may be used as the system 100 including the microflow reactor.

Hereinafter, a method of preparing a secondary amine compound from a primary amine compound and a halide compound using the microflow reactor 100 will be described in detail.

Figure 2:
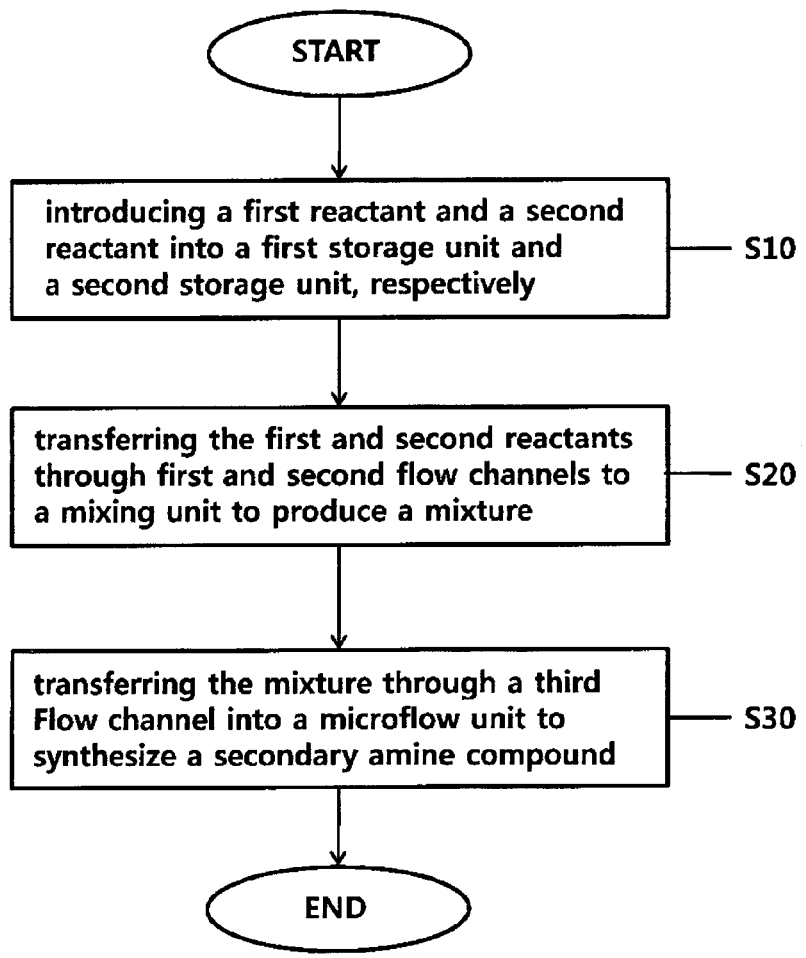
FIG. 2 is a process flow chart illustrating a method of preparing a secondary amine compound according to embodiments of the present invention.

FIG. 2 is a process flow chart showing a method of preparing a secondary amine compound according to embodiments of the present invention.

Referring to FIGS. 1 and 2, a first reactant and a second reactant are introduced respectively into the first storage unit 10 and second storage unit 15 of the system 100 including the microflow reactor (S10).

The first reactant comprises a primary amine compound represented by the following formula (1):

$$R_1\text{—}NH_2 \qquad \text{Formula (1)}$$

wherein $R_1$ is a substituted or unsubstituted, linear or branched $C_1$-$C_6$ alkyl, a substituted or unsubstituted, linear or branched $C_2$-$C_6$ alkenyl, a substituted or unsubstituted $C_3$-$C_6$ cycloalkyl, a substituted or unsubstituted phenyl, or a substituted or unsubstituted naphthalenyl. For example, the primary amine compound represented by formula 1 may be a substituted or unsubstituted butylamine, a substituted or unsubstituted butenylamine, a substituted or unsubstituted pentylamine, a substituted or unsubstituted pentenylamine, or a substituted or unsubstituted aniline.

According to embodiments of the present invention, the primary amine compound may be represented by the following formula (4):

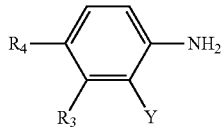

Formula (4)

wherein $R_3$ and $R_4$ are each independently H, a substituted or unsubstituted, linear or branched $C_1$-$C_6$ alkyl, a substituted or unsubstituted $C_2$-$C_3$ alkenyl, a substituted or unsubstituted phenyl, a substituted or unsubstituted naphthalenyl, a linear or branched $C_1$-$C_6$ heteroalkyl group containing at least one of O, N, S and Se, a $C_2$-$C_3$ heteroalkenyl group containing at least one of O, N, S and Se, or a $C_5$-$C_{12}$ heteroaryl group containing at least one of O, N, S and Se, and Y is H, fluoro, chloro, bromo, iodo, nitro, a substituted or unsubstituted phenyl, a substituted or unsubstituted naphthalenyl, or a substituted or unsubstituted, linear or branched $C_1$-$C_6$ alkyl. Preferably, Y may be iodo. For example, the primary amine compound may be iodoaniline.

The second reactant comprises a halide compound represented by the following formula (2):

$$R_2\text{—}X \qquad \text{Formula (2)}$$

wherein $R_2$ is a substituted or unsubstituted, linear or branched $C_1$-$C_6$ alkyl, a substituted or unsubstituted, linear or branched $C_2$-$C_6$ alkenyl, a substituted or unsubstituted benzyl, or a substituted or unsubstituted methyl naphthalene, and X is chloro, bromo or iodo.

According to embodiments of the present invention, $R_2$ may be a unsubstituted, linear or branched $C_1$-$C_6$ alkyl, a linear or branched $C_1$-$C_6$ alkyl substituted with fluoro, chloro, bromo, iodo or nitro, a unsubstituted, linear or branched $C_2$-$C_6$ alkenyl, a linear or branched $C_2$-$C_6$ alkenyl substituted with fluoro, chloro, bromo, iodo or nitro, a unsubstituted benzyl, or a benzyl substituted with fluoro, chloro, bromo, iodo or nitro. For example, $R_2$ may be allyl, butyl, butenyl, pentyl, benzyl or pentenyl, and X may be bromo.

According to embodiments of the present invention, the first and second reactants may further comprise a solvent, such as dimethylformamide, tetrahydrofuran, acetonitrile, methanol, ethanol, isopropanol or isobutanol, which may be used alone or a mixture of two or more thereof. For example, the solvent may be dimethylformamide or tetrahydrofuran.

After adding the primary amine compound represented by formula (1) and the halide compound represented by formula (2) to the first and second storage units 10 and 15, respectively, the solvent may be added to the first and second storage units 10 and 15 to dissolve the primary amine compound and the halide compound.

According to embodiments of the present invention, the first and second reactants may further comprise cesium hydroxide. Cesium hydroxide may be added to and dissolved in each of the first and second storage units 10 and 15 including the primary amine compound and halide compound dissolved in the solvent.

According to embodiments of the present invention, the first and second reactants in the first and second storage units 10 and 15 may comprise the primary amine compound represented by formula (1) and the halide compound represented by formula (2), respectively, at a concentration of 0.001-1 mole. For example, the first and second reactants may comprise the primary amine compound represented by formula (1) and the halide compound represented by formula (2), respectively, at a concentration of 0.002-0.2 moles.

Referring to FIG. 2, the first and second reactants are transferred through the first flow channel 20 and the second flow channel 25 into the mixing unit 30 to produce a mixture (S20).

The first and second flow channels 20 and 25 which have been separated from each other are combined into one channel in the mixing unit 30, so that the first and second reactants are mixed with each other in the mixing unit 30, thereby producing a mixture comprising both the first and second reactants.

According to embodiments of the present invention, the yield of the secondary amine compound (final product) and the production of byproducts can vary depending on the flow rates of the first and second reactants in the first and second flow channels 20 and 25. The flow rates of the first and second reactants in the first and second flow channels 20 and 25 may be 0.01-10 ml/min. For example, the flow rates of the first and second reactants in the first and second flow channels 20 and 25 may be 0.01-5 ml/min. If the flow rates of the first and second reactants are out of the above range, the diffusion rates of the first and second reactants in the first and second flow channels can increase, thus reducing the reaction efficiency.

According to embodiments of the present invention, each of the first and second flow channels may have a length of 1-100 cm. When the first and second flow channels have the above length, the yield of the second amine compound will be high, and the production of byproducts, such as a tertiary amine compound or an ammonium salt, can be effectively reduced.

Referring to FIGS. 1 and 2, the mixture is transferred through the third flow channel 40 into the microflow reactor 45 to synthesize the secondary amine compound (S30).

According to embodiments of the present invention, the yield of the secondary amine compound may vary depending on the flow rate of the mixture (comprising the first and second reactants) in the third flow channel 40. The flow rate of the mixture in the third flow channel 40 may be 0.01-10 ml/min. If the flow rate of the mixture in the third flow channel is out of the above range, the diffusion rate of the mixture in the third flow channel can increase or the reaction efficiency of the first and second reactants in the microflow reactor can decrease. For example, the flow rate of the mixture in the third flow channel 40 may be 0.01-5 ml/min.

According to embodiments of the present invention, the third flow channel may have a length of 1-100 cm. When the third flow channel has the above length, the yield of the secondary amine compound will be high, and the production of byproducts such as a tertiary amine compound or an ammonium salt can be effectively reduced.

The microflow reactor 45 comprises a plurality of microchannels. While the mixture comprising the first and second reactants passes through the microchannels, the first amine compound and the halide compound react with each other to synthesize the secondary amine compound. The arrangement, length and capacity of the microchannels can be suitably controlled depending on the type of reaction that is carried out in the microflow reactor 45.

In the microflow reactor 45, the primary amine compound of formula (1) included in the first reactant reacts with the halide compound of formula (2) included in the second reactant, whereby the secondary amine compound represented by the following formula (3) can be synthesized as a product:

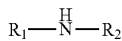

Formula (3)

wherein $R_1$ is a substituted or unsubstituted, linear or branched $C_1$-$C_6$ alkyl, a substituted or unsubstituted, linear or branched $C_2$-$C_6$ alkenyl, a substituted or unsubstituted $C_3$-$C_6$ cycloalkyl, a substituted or unsubstituted phenyl, or a substituted or unsubstituted naphthalenyl, and $R_2$ is a substituted or unsubstituted, linear or branched $C_1$-$C_6$ alkyl, a substituted or unsubstituted, linear or branched $C_2$-$C_6$ alkenyl, a substituted or unsubstituted benzyl, or a substituted or unsubstituted methyl naphthalene.

According to embodiments of the present invention, $R_2$ may be a unsubstituted, linear or branched $C_1$-$C_6$ alkyl, a linear or branched $C_1$-$C_6$ alkyl substituted with fluoro, chloro, bromo, iodo or nitro, a unsubstituted, linear or branched $C_2$-$C_6$ alkenyl, a linear or branched $C_2$-$C_6$ alkenyl substituted with fluoro, chloro, bromo, iodo or nitro, a unsubstituted benzyl, or a benzyl substituted with fluoro, chloro, bromo, iodo or nitro. For example, $R_2$ may be allyl, butyl, butenyl, pentyl, benzyl or pentenyl.

According to embodiments of the present invention, when the primary amine compound included in the first reactant is the compound represented by formula (2), it can react with the halide compound of formula (3) included in the second reactant, thereby forming a secondary amine represented by the following formula (5):

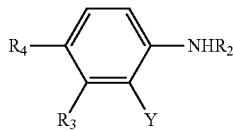

Formula (5)

wherein $R_3$ and $R_4$ are each independently H, a substituted or unsubstituted, linear or branched $C_1$-$C_6$ alkyl, a substituted or unsubstituted $C_2$-$C_3$ alkenyl, a substituted or unsubstituted phenyl, a substituted or unsubstituted naphthalenyl, a linear or branched $C_1$-$C_6$ heteroalkyl group containing at least one of O, N, S and Se, a $C_2$-$C_3$ heteroalkenyl group containing at least one of O, N, S and Se, or a $C_5$-$C_{12}$ heteroaryl group containing at least one of O, N, S and Se, $R_2$ is a substituted or unsubstituted, linear or branched $C_1$-$C_6$ alkyl, a substituted or unsubstituted, linear or branched $C_2$-$C_6$ alkenyl, a substituted or unsubstituted benzyl, or a substituted or unsubstituted methyl naphthalene and Y is H, fluoro, chloro, bromo, iodo, nitro, a substituted or unsubstituted phenyl, a substituted or unsubstituted naphthalenyl, or a substituted or unsubstituted, linear or branched $C_1$-$C_6$ alkyl.

The temperature and pressure of the microflow reactor 45 and the residence time of the first and second reactants in the microflow reactor can be controlled to be suitable for the reaction between the first and second reactants. Thus, if the secondary amine compound is formed from the primary amine compound using the system 100 including the microflow reactor, only one of hydrogen atoms bound to the nitrogen atoms of the primary amine compound will be substituted, so that the production of byproducts such as a tertiary amine compound or an ammonium salt can be reduced and the secondary amine compound can be efficiently prepared.

The first and second reactants are allowed to react with each other in the microflow reactor 45 for 30 seconds to 10 minutes. Depending on the residence time of the first and second reactants in the microflow reactor 45, the yield of the secondary amine compound and the production of byproducts such as a tertiary amine compound or an ammonium salt can be controlled. If the first and second reactants react with each other in the microflow reactor 45 for the above-described time, the secondary amine compound can be obtained in high yield, and the production of byproducts such as a tertiary amine compound or an ammonium salt can be reduced.

The temperature of the microflow reactor 45 may range from −40° C. to 350° C., and preferably from 80° C. to 300° C. Depending on the temperature of the microflow reactor 45, the yield of secondary amine compound produced and the production of byproducts such as a tertiary amine compound or an ammonium salt can be controlled. If the temperature of the microflow reactor 45 is out of the above-specified range, the yield of the secondary amine compound can be reduced.

The pressure of the microflow reactor 45 may range from atmospheric pressure to 25 bar, and preferably from atmospheric pressure to 10 bar. The pressure of the microflow reactor 45 can be controlled by the control unit 55.

The secondary amine compound produced in the microflow reactor 45 is passed through the fourth flow channel 50, the control unit 55 and the fifth flow channel 60 and collected in the collection unit 65.

According to the inventive method for preparing the secondary amine compound, the reaction is carried out using the microflow reactor, so that the reaction conditions can be accurately controlled. Accordingly, the production of byproducts such as a tertiary amine compound or an ammonium salt can be minimized, and thus the secondary amine compound can be efficiently produced from the primary amine compound.

MODE FOR THE INVENTION

Example 1

Preparation 1 of N-allyl-2-iodoaniline Using Microflow Reactor

N-benzyl-2-iodoaniline was prepared using a system (FRX 200, Syrris Limited) including a microflow reactor. For this purpose, 329 mg (1.5 mmol) of 2-iodoaniline and 15 ml of dimethylformamide were added to the first storage unit of the system including the microflow reactor to dissolve the 2-iodoaniline, and then 112 mg (0.75 mmol) of cesium hydroxide was added thereto. Meanwhile, 156 μl (1.8 mmol) of allyl bromide and 15 ml of dimethylformamide were added to the second storage unit of the system, and then 112 mg (0.75 mmol) of cesium hydroxide was added thereto. The reactants included in the first and second storage units were transferred through the first and second flow channels to the mixing unit, and then transferred to the microflow reactor including microchannels through the third flow channel. The first and second flow channels could transfer 5 ml (2.5 ml for each flow channel) of the reactants to the microflow reactor. The microflow reactor was set at a capacity of 1 ml, a temperature of 236° C. and a pressure of 7 bar. The reactants in the first and second reactants were set such that they were passed through the first to third flow channels at a flow rate of 0.4 ml/min and introduced into the microflow reactor. Also, the residence time of the reactants in the microflow reactor was set to 2.5 minutes.

1 ml of the product, transferred from the microflow reactor into the collection unit, was collected and diluted in 2 ml of dichloromethane, and the organic layer was washed 6 times or more with 1 ml of water and brine. The organic layer was separated and dried with magnesium sulfate, after which the solvent was removed, and the residue was analyzed by HPLC (Agilent 1200 series, Aglient Technology).

As a result, the residue contained 49 wt % of N-allyl-2-iodoaniline, 1 wt % of N,N-diallyl-2-iodoaniline, 32 wt % of unreacted 2-iodoaniline and a balance of reaction byproducts.

Example 2

Preparation 2 of N-allyl-2-iodoaniline Using Microflow Reactor

The procedure of Example 1 was repeated, except that the temperature of the microflow reactor, the flow rate of the reactants in the first and third flow channels, and the residence time of the reactants in the microflow reactor were set at 153° C., 0.2 ml/min and 5 minutes, respectively. The residue was collected and analyzed. As a result, the residue contained 31 wt % of N-allyl-2-iodoaniline, 0 wt % of N,N-diallyl-2-iodoaniline, 51 wt % of unreacted 2-iodoaniline and a balance of reaction byproducts.

Example 3

Preparation 3 of N-allyl-2-iodoaniline Using Microflow Reactor

The procedure of Example 1 was repeated, except that the temperature of the microflow reactor, the flow rate of the reactants in the first and third flow channels, and the residence time of the reactants in the microflow reactor were set at 236° C., 1 ml/min and 1 minute, respectively. The residue was collected and analyzed. As a result, the residue contained 40 wt % of N-allyl-2-iodoaniline, 0 wt % of N,N-diallyl-2-iodoaniline, 43 wt % of unreacted 2-iodoaniline and a balance of reaction byproducts.

Example 4

Preparation 1 of N-benzyl-2-(3,4-dimethoxyphenyl)ethylamine Using Microflow Reactor N-benzyl-2-(3,4-dimethoxyphenyl)ethylamine was prepared using a system (FRX200, Syrris Limited) including a microflow reactor. For this purpose, 83 μl (0.5 mmol) of 2-(3,4-dimethoxyphenyl)ethylamine and 5 ml of tetrahydrofuran were added to the first storage unit of the system including the microflow reactor, and then 70 μl (0.5 mmol) of triethylamine was added thereto. Meanwhile, 60 μl (0.5 mmol) of benzyl bromide and 5 ml of tetrahydrofuran were added to the second storage unit of the system. The reactants included in the first and second storage units were transferred through the first and second flow channels to the mixing unit, and then transferred through the third flow channel into the microflow reactor including microchannels. The first and second flow channels could transfer 360 μl (180 μl for each flow channel) of the reactants to the microflow reactor. The microflow reactor was set at a capacity of 250 μl, a temperature of 100° C. and a pressure of 8 bar. The reactants in the first and second storage units were set such that they were passed through the first to third flow channels at a flow rate of 0.05 ml/min and introduced into the microflow reactor. Also, the residence time of the reactants in the microflow reactor was set at 2.5 minutes.

300 μl of the product, transferred from the microflow reactor to the collection unit, was collected, filtered through a membrane filter, and then diluted in 0.5 ml of acetonitrile.

The resulting solution was analyzed by HPLC.

As a result, the residue contained 31 wt % of N-benzyl-2-(3,4-dimethoxyphenyl)ethylamine, 2 wt % of N,N-dibenzyl-2-(3,4-dimethoxyphenyl)ethylamine, unreacted 2-(3,4-dimethoxyphenyl)ethylamine, and a balance of reaction byproducts.

Example 5

Preparation of N-benzyl-3,5-dimethoxyaniline Using Microflow Reactor

N-benzyl-3,5-dimethoxyaniline was prepared using a system (FRX200, Syrris Limited) including a microflow reactor. For this purpose, 76 mg (0.5 mmol) of 3,5-dimethoxyaniline and 5 ml of dimethylformamide were added to the first storage unit of the system including the microflow reactor, and then 70 μl (0.5 mmol) of triethylamine was added thereto. Meanwhile, 60 μl (0.5 mmol) of benzyl bromide and 5 ml of dimethylformamide were added to the second storage unit of the system. The reactants included in the first and second storage units were transferred through the first and second flow channels to the mixing unit, and then transferred through the third flow channel into the microflow reactor including microchannels. The first and second flow channels could transfer 360 μl (180 μl for each flow channel) of the reactants to the microflow reactor. The microflow reactor was set at a capacity of 250 μl, a temperature of 225° C. and a pressure of 8 bar. The reactants in the first and second storage units were set such that they were passed through the first to third flow channels at a flow rate of 0.05 ml/min and introduced into the microflow reactor. Also, the residence time of the reactants in the microflow reactor was set at 2.5 minutes.

100 μl of the product, transferred from the microflow reactor to the collection unit, was collected, and then diluted in 2.5 ml of acetonitrile.

The resulting solution was analyzed by HPLC.

As a result, the solution contained 44 wt % of N-benzyl-3,5-dimethoxyaniline, 4 wt % of N,N-dibenzyl-3,5-dimethoxyaniline, 35 wt % of unreacted 3,5-dimethoxyaniline and a balance of reaction byproducts.

COMPARATIVE EXAMPLE 1

Preparation of N-allyl-2-iodoaniline in Flask 53.7 mg (0.245 mmol) of 2-iodoaniline and 2 ml of the dimethylformaldehyde were added to a 25-ml flask, and then the 2-iodoaniline was dissolved. Next, 25 μl (0.294 mmol) of allyl bromide and 36.8 mg (0.245 mmol) of cesium hydroxide were added thereto, and the solution was stirred at room temperature for 3 hour. 10 μl of dichloromethane was added to the stirred solution, and then the organic layer was washed 6 times or more with 5 μl of water and brine. The organic layer was separated, and then dried with magnesium sulfate. After the solvent has been removed by vacuum distillation, the residue was analyzed by fresh column chromatography (n-hexane: ethyl acetate=20:1 (v/v)) and HPLC. The results of the analysis by fresh column chromatography indicated that the residue contained 39 wt % of N-allyl-2-iodoaniline and 5 wt % of N,N-diallyl-2-iodoaniline. Meanwhile, the results of the HPLC analysis indicated that the residue contained 47 wt % of N-allyl-2-iodoaniline and 8 wt % of N,N-diallyl-2-iodoaniline.

COMPARATIVE EXAMPLE 2

Preparation of N-benzyl-2-(3,4-dimethoxyphenyl)ethylamine in Flask

83 μl (0.5 mmol) of 2-(3,4-dimethoxyphenyl)ethylamine and 5 ml of tetrahydrofuran were added to a 25-ml flask, and then 70 μl (0.5 mmol) of triethylamine was added thereto. Then, 60 μl (0.5 mmol) of benzyl bromide was added thereto, and the solution was stirred in a reflux heater at 66° C. for 3 hours. Then, 300 μl of the reaction product was collected, filtered through a membrane filter, and then diluted in 0.5 ml of acetonitrile.

The resulting solution was analyzed by HPLC.

As a result, the residue contained 26 wt % of N-benzyl-2-(3,4-dimethoxyphenyl)ethylamine, 6 wt % of N,N-dibenzyl-2-(3,4-dimethoxyphenyl)ethylamine, unreacted 2-(3,4-dimethoxyphenyl)ethylamine, a balance of reaction byproducts.

COMPARATIVE EXAMPLE 3

Preparation of N-benzyl-3,5-dimethoxyaniline in Flask 76 mg (0.5 mmol) of 3,5-dimethoxyaniline and 5 ml of dimethylformamide were added to a 25-ml flask, and then 70 μl (0.5 mmol) of triethylamine was added thereto. Next, 60 μl (0.5 mmol) of benzyl bromide was added thereto, and the solution was stirred in a reflux heater at 125° C. for 30 minutes.

100 μl of the reaction product was collected and dilited in 2.5 ml of acetonitrile.

The resulting solution was analyzed by HPLC.

As a result, the solution contained 37 wt % of N-benzyl-3,5-dimethoxyaniline, 20 wt % of N,N-dibenzyl-3,5-dimethoxyaniline, 10 wt % of unreacted 3,5-dimethoxyaniline and a balance of reaction byproducts.

As can be seen from the results of Examples 1 to 5 and Comparative Examples 1 to 3 above, in the case of Examples 1 to 5, a tertiary amine compound such as N,N-diallyl-2-iodoaniline was less produced than in the case of Comparative Examples or was not produced. This suggests that, in the case in which the secondary amine compound is prepared from the primary amine compound using the microflow reactor, byproducts such as a tertiary amine compound are less produced than in the case in which the secondary amine compound is produced in a flask.

The invention claimed is:

1. A method of preparing a secondary amine compound, the method comprising:
   mixing a first reactant comprising a primary amine compound represented by formula (4)

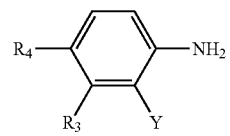

Formula (4)

and cesium hydroxide with a second reactant comprising a halide compound represented by formula (2)

$R_2$—X    Formula (2)

and cesium hydroxide, thereby producing a mixture; and
   introducing the mixture into a microflow reactor through flow channels, thereby synthesizing a secondary amine compound represented by formula (5)

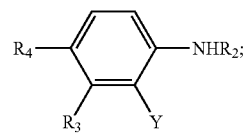

Formula (5)

wherein $R_2$ is a linear or branched $C_2$-$C_6$ alkenyl, $R_3$ and $R_4$ are H, X is chloro, bromo or iodo, and Y is iodo.

2. The method of claim 1, wherein $R_2$ in formula (2) is allyl, butenyl, or pentenyl, and X is bromo.

3. The method of claim 1, wherein the first and second reactants comprise at least one solvent selected from the group consisting of dimethylformamide, tetrahydrofuran, acetonitrile, methanol, ethanol, isopropanol and isobutanole.

4. The method of claim 1, wherein the producing of the mixture comprises:
   introducing the first reactant and the second reactant into storage units; and
   transferring the first reactant and the second reactant from the storage units to a mixing unit.

5. The method of claim 1, wherein the microflow reactor has a temperature ranging from 80° C. to 300° C.

6. The method of claim 1, wherein the flow rate of the mixture in each of the flow channels is 0.01-10 ml/min.

7. The method of claim 1, wherein the first and second reactants react with each other in the microflow reactor for 30 seconds to 10 minutes.

8. The method of claim 1, wherein each of the flow channels has a length of 1-100 cm.

* * * * *